(12) United States Patent
Ohi (10) Patent No.: US 9,820,710 B2
(45) Date of Patent: Nov. 21, 2017

(54) RADIATION TOMOGRAPHY APPARATUS

(75) Inventor: Junichi Ohi, Muko (JP)

(73) Assignee: Shimadzu Corporation, Kyoto (JP)

( * ) Notice: Subject to any disclaimer, the term of this patent is extended or adjusted under 35 U.S.C. 154(b) by 35 days.

(21) Appl. No.: 14/124,578

(22) PCT Filed: Jun. 8, 2011

(86) PCT No.: PCT/JP2011/003228
§ 371 (c)(1),
(2), (4) Date: Dec. 6, 2013

(87) PCT Pub. No.: WO2012/168972
PCT Pub. Date: Dec. 13, 2012

(65) Prior Publication Data
US 2014/0119505 A1    May 1, 2014

(51) Int. Cl.
| | | |
|---|---|---|
| *G01J 1/42* | (2006.01) | |
| *G01T 1/00* | (2006.01) | |
| *G01T 1/16* | (2006.01) | |
| *A61B 6/00* | (2006.01) | |
| *A61B 6/03* | (2006.01) | |

(Continued)

(52) U.S. Cl.
CPC .............. *A61B 6/502* (2013.01); *A61B 6/037* (2013.01); *A61B 6/4233* (2013.01); *A61B 6/461* (2013.01); *A61B 6/5205* (2013.01); *A61B 6/5211* (2013.01); *G01T 1/2985* (2013.01); *A61B 6/04* (2013.01); *A61B 6/0492* (2013.01); *A61B 6/107* (2013.01); *A61B 6/4208* (2013.01);

(Continued)

(58) Field of Classification Search
USPC ....... 250/363.01, 361 R, 362, 363.04, 370.1, 250/395
See application file for complete search history.

(56) References Cited

U.S. PATENT DOCUMENTS

| | | | |
|---|---|---|---|
| 2008/0181355 A1* | 7/2008 | Hemmendorff et al. | 378/4 |
| 2010/0027866 A1* | 2/2010 | Ohi | 382/131 |

(Continued)

FOREIGN PATENT DOCUMENTS

| | | |
|---|---|---|
| JP | 2002-365239 A | 12/2002 |
| JP | 2009-300319 A | 12/2009 |
| JP | 2010-038594 A | 2/2010 |

OTHER PUBLICATIONS

Office Action Chinese Patent Application No. 201180070995.3 dated Feb. 16, 2015.

(Continued)

*Primary Examiner* — David Porta
*Assistant Examiner* — Carolyn Igyarto
(74) *Attorney, Agent, or Firm* — McDermott Will & Emery LLP (57) ABSTRACT

Provided is a preview image generating section configured to generate preview image during radiography for the purpose of providing a radiation tomography apparatus that allows suppression of unnecessary imaging time by displaying a condition of an image during the radiography in the process of diagnosis. An operator can recognize from the preview image how a subject appears in the image in a radiation tomography apparatus also during the radiography. This allows stopping the radiography before a diagnostic image having a suitable level of clearness for diagnosis is generated. As a result, a shorter imaging time is achieved, and burden to the subject can be suppressed.

7 Claims, 4 Drawing Sheets

(51) Int. Cl.
*G01T 1/29* (2006.01)
*G01T 1/164* (2006.01)
*A61B 6/04* (2006.01)
*G01T 1/20* (2006.01)
*G06T 11/00* (2006.01)
*A61B 6/10* (2006.01)

(52) U.S. Cl.
CPC .......... *G01T 1/1641* (2013.01); *G01T 1/2006* (2013.01); *G06T 11/005* (2013.01); *G06T 11/008* (2013.01); *G06T 2207/30068* (2013.01); *G06T 2207/30204* (2013.01); *G06T 2211/40* (2013.01); *Y10S 378/901* (2013.01)

(56) References Cited

U.S. PATENT DOCUMENTS

2010/0252743 A1* 10/2010 Ogawa ................ A61B 6/4233
 250/370.08
2012/0059244 A1* 3/2012 McClelland et al. ......... 600/414

OTHER PUBLICATIONS

International Search Report, w/ English translation thereof, issued in International Application No. PCT/JP2011/003228 dated Jul. 5, 2011.

* cited by examiner

Prior art

RADIATION TOMOGRAPHY APPARATUS

RELATED APPLICATIONS

This application is the U.S. National Phase under 35 U.S.C. §371, of International Application No. PCT/JP2011/003228, filed on Jun. 8, 2011, the disclosure of which Application is incorporated by reference herein.

TECHNICAL FIELD

The present invention relates to a radiation tomography apparatus configured to detect annihilation radiation emitted from a subject to image distribution of radiopharmaceutical within the subject. Particularly, the present invention is directed to a radiation tomography apparatus for diagnosis for cancer.

BACKGROUND ART

Medical institutions are equipped with a radiation tomography apparatus that allows imaging of radiopharmaceutical distribution as described in, for example, Patent Literature 1. Description will be given of a detailed construction of such a radiation tomography apparatus. The conventional radiation tomography apparatus includes a radiation ring having radiation detectors arranged circularly for detecting radiation. The detector ring detects a pair of radiation (an annihilation radiation-pair) having opposite directions to each other that is emitted from radiopharmaceutical within a subject.

Figure 8:
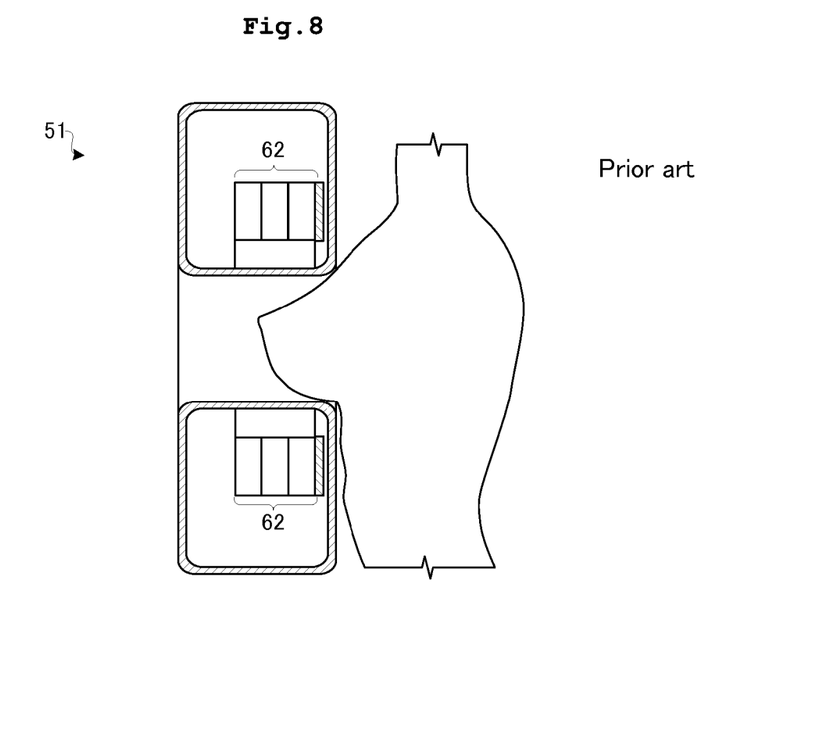
FIG. 8 is a schematic view illustrating a conventional radiation tomography apparatus.

A type of such the radiation tomography apparatus includes a radiation tomography apparatus for breast inspections. Description will be given in detail of the radiation tomography apparatus for breast inspections. FIG. 8 illustrates a conventional radiographic apparatus for breast inspections. A conventional radiographic apparatus 51 for breast inspections guides one breast of a subject into a detector ring 62. The detector ring 62 detects annihilation radiation-pairs emitted from the subject under this condition.

The detector ring 62 identifies generating sources of the annihilation radiation-pairs emitted from the breast, thereby generating radiopharmaceutical distribution in accordance with positional information on the generating sources. The more radiopharmaceutical is likely to be accumulated in cancerous tissue rather than normal tissue. Consequently, checking the radiopharmaceutical distribution allows diagnosis for breast cancer.

A diagnosing method is to be described in detail. Firstly, a breast of a subject is set in a radiation tomography apparatus. Secondary, detection of an annihilation radiation-pair starts. The annihilation radiation-pair is continuously detected until a satisfactory number of beams of annihilation radiation for image generation is detected. When a satisfactory number of beams of annihilation radiation is obtained, detection of the annihilation radiation-pair is completed. Then, a tomographic image having the breast of the subject appearing therein is generated in accordance with the accumulated detection data.

CITATION LIST

Japanese Patent Publication No. 2009-300319A

SUMMARY OF INVENTION

Technical Problem

The conventional radiographic apparatus, however, has the following problem. Specifically, with the conventional radiographic apparatus, it is unclear what types of tomographic images are to be obtained until completion of detecting the annihilation radiation-pairs. Such a problem may arise.

Since the breast is soft, the breast has a non-uniform shape when being guided into the detector ring 62. The breast also has a non-uniform depth into the detector ring 62. Consequently, a tomographic image may be taken while the breast is not satisfactorily contained in the detector ring. As noted above, when the annihilation radiation-pair is detected while a portion of the breast on a trunk side adjacent to a chest wall is not completely contained in the detector ring 62, a tomographic image to be generated may have no image of the breast on a chest wall side appearing therein. This means a possibility that when the breast on the chest wall side is a site of interest for diagnosis, a tomographic image may be generated with the site of interest not appearing in the field of view.

Then, when the breast of the subject does not satisfactorily appear in the generated tomographic image, the diagnosis has to be conducted again from detection of an annihilation radiation-pair. However, it is not easy to conduct the diagnosis again. This is because not a few number of annihilation radiation-pairs has to be detected for tomographic image generation, and thus the tomographic image generation is time-consuming. If the time-consuming diagnosis is proved to be in vain, the subject bears a large burden.

The present invention has been made regarding the state of the art noted above, and its object is to provide a radiation tomography apparatus that allows suppression of unnecessary imaging time by displaying a condition of an image during radiography also in the process of diagnosis.

Solution to Problem

This invention is constituted as stated below to achieve the above object. One aspect of the present invention discloses a radiation tomography apparatus including a detector ring having radiation detectors for detecting radiation being arranged annularly; a preview image generating device configured to generate a preview image successively in accordance with detection data from the detector ring, the preview image having a generating source of an annihilation radiation-pair mapped therein; a display device configured to display the preview image; an input device configured to input an operator's command; and a diagnostic image generating device configured to map the generating source of the annihilation radiation-pair to generate a diagnostic image. When a command to stop radiography and a command to resume radiography are issued to the input device, the diagnostic image generating device generates the diagnostic image without using the detection data obtained before the command to resume radiography is issued.

Operation and Effect

The embodiment of the present invention includes the preview image generating device configured to generate the preview image during radiography. An operator can recognize from the preview image how the subject appears in the image in the radiation tomography apparatus also during the radiography. When the subject fails to be in a position of the field of view suitable for diagnosis, the operator can issue the commands to stop and resume the radiography via the input device. This allows stopping the radiography before a diagnostic image having a suitable level of clearness for diagnosis is generated, and allows resuming radiography of the diagnostic image after aligning the subject. Consequently, diagnosis with higher accuracy can be conducted, and a shorter additional imaging time is achieved even when radiography is conducted again. As a result, a radiation tomography apparatus having suppressed burden to the subject can be provided.

Moreover, it is more preferable that the diagnostic image generating device of the radiation tomography apparatus generates the diagnostic image also using the detection data that the preview image generating device has been used for generating the preview image.

Operation and Effect

With the foregoing construction, the diagnostic image generating device generates the diagnostic image also using the detection data that the preview image generating device has been used for generating the preview image. This increases a number of pieces of detection data as much as possible upon generating the diagnostic image, achieving the radiation tomography apparatus that allows generating a clearer diagnostic image.

Moreover, it is more preferable that the preview image generating device of the radiation tomography apparatus generates the preview image by mapping the generating source of the annihilation radiation-pair detected during an image generation time, and that the preview image generating device successively generates the preview image for every image generation time.

Operation and Effect

With the foregoing construction, the preview image is updated for every image generation time. Such the construction allows the operator to recognize sequentially how the subject appears in the field of view of the radiation tomography apparatus currently. This enables early recognition of a radiography area.

Moreover, it is more preferable that the preview image generating device of the radiation tomography apparatus has the image generation time of one second to one minute.

Operation and Effect

The foregoing construction represents a detailed construction of the radiation tomography apparatus according to the present invention. That is, an image generation time of one second to one minute allows provision of the radiation tomography apparatus in harmony with throughput of image generation and convenience of an operator.

Moreover, it is more preferable that the preview image generating device of the radiation tomography apparatus generates the preview image from the detection data by a statistical reconstruction technique, and that a number of subsets in the form of a parameter in the statistical reconstruction technique is in a range of 2 to 600, and a number of occurrences representing iteration is in a range of 1 to 16.

Operation and Effect

The foregoing construction represents a detailed construction of the radiation tomography apparatus according to the present invention. In the statistical reconstruction technique by the preview image generating device, a number of subsets in the form of a parameter is in a range of 2 to 600, and a number of occurrences (iteration) is in a range of 1 to 16. This allows provision of the radiation tomography apparatus in harmony with throughput of image generation and convenience of an operator.

Moreover, it is more preferably that the radiation tomography apparatus further includes a marker attached to the subject and configured to absorb radiation.

Operation and Effect

The foregoing construction represents a detailed construction of the radiation tomography apparatus according to the present invention. The construction with the marker attached to the subject allows the operator to recognize a position of the subject in the field of view of the radiation tomography apparatus easily by merely checking how the marker appears in the preview image.

Moreover, the radiation tomography apparatus is preferably used for breast inspections.

Operation and Effect

The foregoing construction represents a detailed construction of the radiation tomography apparatus according to the present invention. The breast is soft and thus has a non-uniform shape. In addition, the breast inspection adopts a mode of guiding the subject partially into the detector ring to obtain a tomographic image. Accordingly, the mode has a possibility of failing to guide the breast of the subject into the radiation tomography apparatus suitably, the possibility being higher than a radiation tomography apparatus guiding a subject entirely into the detector ring. Consequently, application of the construction of the present invention to the radiation tomography apparatus for breast inspections achieves radiography of the breast suitably and efficiently.

Advantageous Effects of Invention

The embodiment of the present invention includes the preview image generating device configured to generate the preview image during radiography. An operator can recognize from the preview image how the subject appears in the image in the radiation tomography apparatus also during the radiography. When the subject fails to be in a position of the field of view suitable for diagnosis, the operator can stop radiation detection by the detector ring via the input device. This allows stopping the radiography before a diagnostic image having a suitable level of clearness for diagnosis is generated, and allows resuming radiography of the diagnostic image after aligning the subject. Consequently, diagnosis with higher accuracy can be conducted, and a shorter additional imaging time is achieved even when radiography is conducted again. As a result, a radiation tomography apparatus having suppressed burden to the subject can be provided.

DETAILED DESCRIPTION

Each embodiment will be described hereinafter as the best mode for carrying out the present invention.

Embodiment 1

Figure 1:
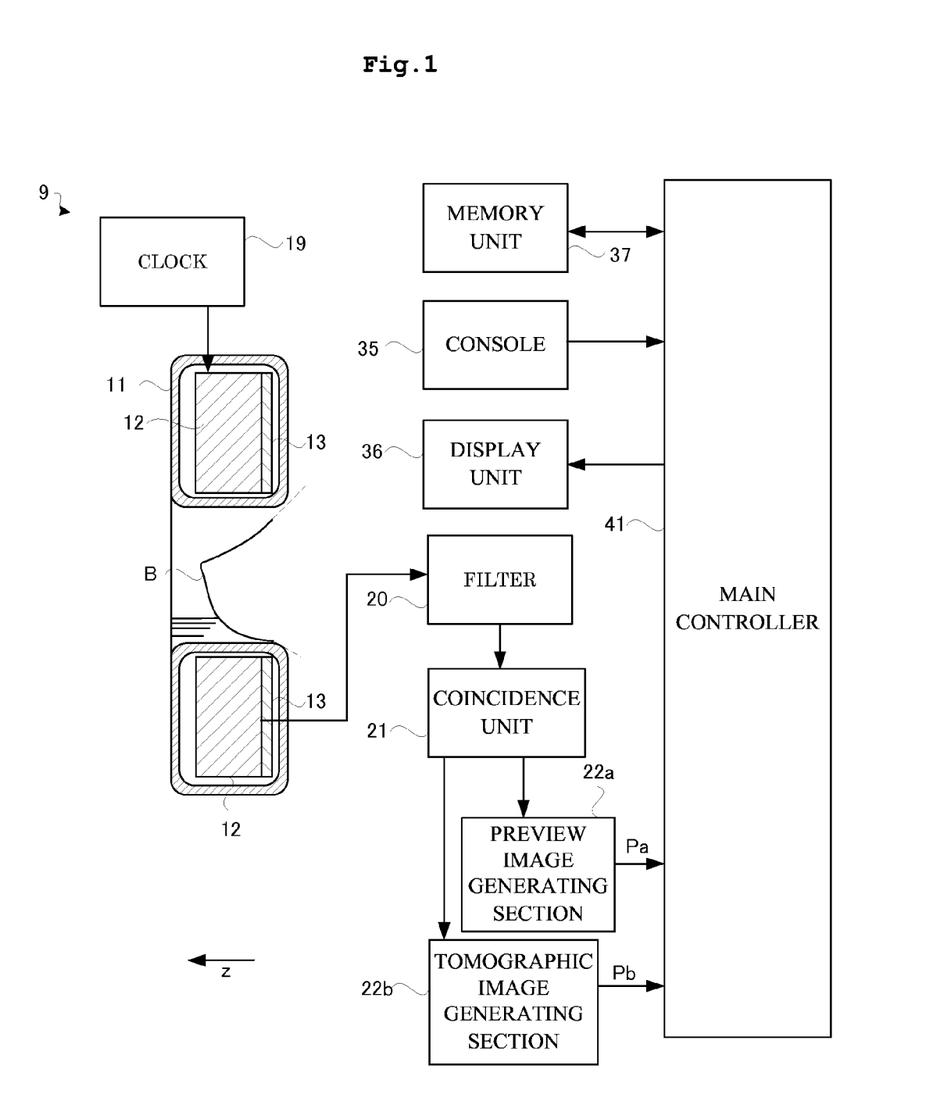
FIG. 1 is a function block diagram of a radiation tomography apparatus according to Embodiment 1.

Embodiments of a radiation tomography apparatus according to the present invention will be described hereinafter with reference to the drawings. Gamma rays in Embodiment 1 are an example of radiation in the present invention. Embodiment 1 has a configuration of a Mammography device for breast inspections. FIG. 1 is a function block diagram illustrating a radiation tomography apparatus according to Embodiment 1. The radiation tomography apparatus 9 according to Embodiment 1 includes a gantry 11 configured to guide a breast B of a subject M in a z-direction, and a detector ring 12 in a ring shape configured to guide the breast B of the subject M inside the gantry 11 in the z-direction. The detector ring 12 has an inner hole in a cylindrical shape (strictly, in a regular octagonal prismatic shape) that extends in the z-direction. Accordingly, the detector ring 12 itself also extends in the z-direction. Here, the inner hole of the detector ring 12 corresponds to a field of view of the radiation tomography apparatus 9 where a tomographic image Pb can be generated. The z-direction extends along a direction where the center axis of the detector ring 12 extends.

A shielding plate 13 is composed of, for example, Tungsten or lead. Radiopharmaceutical exists in a portion other than the breast B of the subject M, from which an annihilation gamma-ray pair is also generated. When such the annihilation gamma-ray pair generated from the portion other than the site of interest enters into the detector ring 12, this is obstructive to radiography of the tomographic image. As a result, the shielding plate 13 in a ring shape is provided so as to cover one end of the detector ring 12 adjacent to the subject M in the z-direction.

A clock 19 sends out temporal information in the form of serial numbers to the detector ring 12. The temporal information representing time of detecting gamma-rays is given to the detection data outputted from the detector ring 12, and the detection data is inputted into a filter 20 to be mentioned later.

Description will be given of the detector ring 12. One unit ring is constituted by arranging eight radiation detectors 1 in an imaginary circle on a plane orthogonal to the z-direction (i.e., a central axis direction). Three unit rings are arranged in the z-direction to form the detector ring 12.

Figure 2:
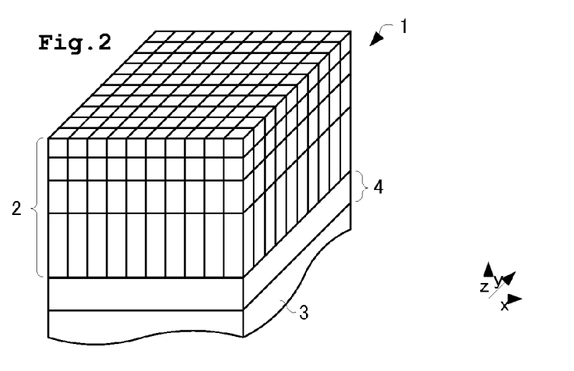
FIG. 2 is a perspective view illustrating a radiation detector according to Embodiment 1.

Brief description will be given of the radiation detector 1. FIG. 2 is a perspective view illustrating the radiation detector according to Embodiment 1. As illustrated in FIG. 2, the radiation detector 1 includes a scintillator 2 configured to convert radiation into light, and a light detector 3 constituted by a photomultiplier tube and detecting the light fluorescence. A light guide 4 is provided between the scintillator 2 and the light detector 3 for receiving light.

The scintillator 2 includes scintillator crystals arranged three-dimensionally. Each of the scintillation counter crystals C is composed of Ce-doped $Lu_{2(1-X)}Y_{2X}SiO_5$ (hereinafter referred to as LYSO). The light detector 3 allows determination about which scintillation counter crystal emits light as well as intensity of light and time when light is generated. Here, the scintillator 2 having the configuration of Embodiment 1 is only exemplification of an aspect that may be adopted. Consequently, the configuration of the present invention is not limited to this.

The detection data outputted from the detector ring 12 is sent to a coincidence unit 21 (see FIG. 1) via a filter 20, to be mentioned later. Two gamma-rays coincidentally enter into the detector ring 12. Here, the two gamma-rays is an annihilation gamma-ray pair derived from the radiopharmaceutical within the subject. The coincidence unit 21 counts a frequency of detecting the annihilation gamma-ray pair for every combination of two of the scintillator crystals constituting the detector ring 12, and sends the resultant to a tomographic image generating section 22b. A positional relationship between the scintillator crystals upon coincidence represents a position and a direction of entering the annihilation gamma-ray pair into the detector ring 12, and thus is information necessary for mapping the radiopharmaceutical. The frequency and energy intensity of the annihilation gamma-ray pair stored for every combination of the scintillator crystals represents variations in generation of the annihilation gamma-ray pair within the subject, and is information necessary for mapping of the radiopharmaceutical. Here, temporal information that the clock 19 gives to the detection data is used for determination of coincident property of the detection data by the coincidence unit 21.

The filter 20 is provided for avoiding sending unnecessary data in the detector ring 12 to the coincidence unit 21. The coincidence unit 21 has to process enormous volumes of data, and thus easily undergoes load. The filter 20 allows thinning of the detection data so as to reduce the load on the coincidence unit 21. For instance, the filter 20 abandons all the detection data when the subject M fails to be guided into the detector ring 12 or the detection data of scattered radiation has small intensity of gamma-rays, and thus inputs none of the detection data into the coincidence unit 21. A group of sets of data with positional data on a line segment connecting the scintillator crystals, data on detection intensity of fluorescence, and data on the detection time being in association with one another is referred to as list data. The list of data is outputted from the filter 20.

A preview image generating section 22a has an important part in the present invention. Description will be given of the preview image generating section 22a. The preview image generating section 22a receives the list data from the filter 20, and generates the preview image successively in accordance with the list data. The preview image indicates a position of the breast B of the subject in a radiographic area of the tomographic image Pb. The preview image has a mapped generating source of an annihilation gamma-ray pair in the inner hole of the detector ring 12. The preview image is not so clear for suitable diagnosis, but is satisfactory for roughly recognizing distribution of radiopharmaceutical within the breast B of the subject. The preview image generating section 22a corresponds to the preview image generating device in the present invention.

Figure 3:
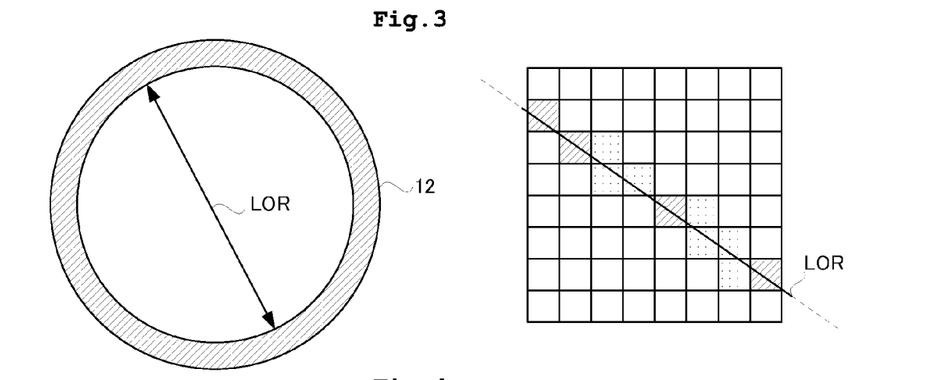
FIG. 3 is a schematic view illustrating an LOR according to Embodiment 1.

Description will be given of an LOR having a relationship with operations of the preview image generating section 22a. FIG. 3 illustrates an LOR (Line of Response) on the left thereof. As illustrated in FIG. 3, the LOR is a line segment connecting two parts of the detector ring 12 where gamma-rays are detected coincidentally. Gamma-rays enter into the two different parts of the detector ring 12 coincidentally. This means that the two gamma-rays are an annihilation gamma-ray pair. Consequently, a generation point (annihilation point) of the annihilation gamma-ray pair is located at any point on the line segment of the LOR. Here, the annihilation point is concentrated in a portion where the radiopharmaceutical is distributed with high density. Taking this into consideration, mapping distribution of the annihilation point causes obtainment of an image representing radiopharmaceutical distribution.

As illustrated on the right of FIG. 3, the preview image generating section 22a recognizes the inner hole of the detector ring 12 as a space divided into a three-dimensional lattice form. Since the inner hole of the detector ring 12 is cylindrical, the space recognized by the preview image generating section 22a is a cylindrical space divided three-dimensionally. FIG. 3 illustrates on the right thereof a partial space recognized by the preview image generating section 22a. The preview image generating section 22a overlaps the LOR representing the list data on the space. Accordingly, the LOR on the right of FIG. 3 crosses a plurality of divided sections.

The preview image generating section 22a gives a large evaluation value to a divided section containing a long LOR, and gives a small evaluation value to a divided section containing a short LOR. That is, the diagonally shaded divided sections on the right of FIG. 3 each contain a long LOR, and thus a large evaluation value is given to these divided sections. The shaded divided sections on the right of FIG. 3 each contain a shorter LOR, and thus a smaller evaluation value is given to these divided sections. The preview image generating section 22a stores the evaluation values of the divided sections such that the values each correspond to the position in the inner hole of the detector ring 12. The preview image generating section 22a calculates the evaluation values for a plurality of LORs to add the evaluation values. Accordingly, since more LORs extend from a portion inside the detector ring 12 having a high concentration of radiopharmaceutical, a total evaluation value of the portion is larger than a portion having a lower concentration of radiopharmaceutical. The preview image generating section 22a repeatedly performs such an operation to obtain three-dimensional data with the generation points of the annihilation gamma-ray pairs mapped therein.

Figure 4:
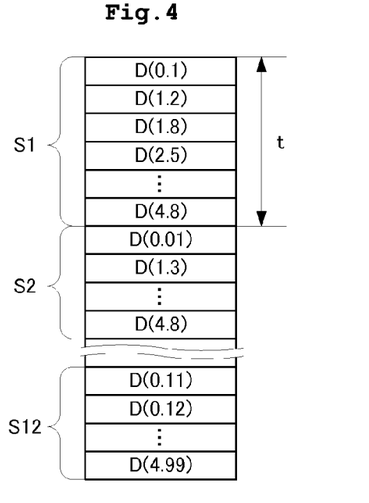
FIG. 4 is a schematic view illustrating a number of subsets according to Embodiment 1.

The data collected in a shorter time is used for the preview image. Consequently, a sufficient number of counts for the reconstructed image cannot be stored, and therefore statistical noises become large. Then, the construction of Embodiment 1 adopts a successive approximation reconstruction method as a statistical reconstruction technique with less influence of the statistical noise. Specifically, a technique such as a list mode OSEM (Ordered Subset expectation maximization) is adopted. That is, the list mode OSEM is a technique for determining radiopharmaceutical distribution to obtain the highest reliability under assumption that the radiopharmaceutical distribution follows specified distribution such as Poisson distribution. This technique is performed by dividing the obtained list mode data by every image generation time t set in advance to perform successive approximation reconstruction and to repeatedly perform image correction. The number m of this division represents a number of subsets. FIG. 4 illustrates the list mode data. FIG. 4 illustrates an image generation time t of 5 seconds and an imaging time of 60 seconds. Consequently, the number of subsets is 12. Here, data regions divided by the number of subsets are each denoted by S1 to S12. Data obtained at a point in time of 0.1 second within the image generation time t is denoted by D(0.1) in a table of the drawing. Since the image generation time t is 5 seconds, a point in time for obtaining the data is in a range of 0 to 5 seconds. The image generation time t in Embodiment 1 is variable from 1 second to 600 seconds. Accordingly, the number of subsets is in a range of 2 to 600, and a repetition number (iteration) is in a range of 1 to 16.

The above number of subsets may be determined by dividing an expected total number of counts by a number of image generation counts. The expected total number of counts is an expected value of a total number of counts obtained during inspections. The number of image generation counts is a number of counts CT used for image generation.

The preview image generating section 22a calculates an evaluation value for each of data regions S1 to S6. For instance, when calculation of the evaluation value is performed to a data region S1 obtained for 5 seconds from starting collection of data, the calculation of the evaluation value is performed only to rectangular divided sections on the data region S1 as illustrated on the right of FIG. 3. Upon completion of the calculation of the evaluation value on the data region S1, the preview image generating section 22a calculates evaluation values on the data regions S2 and S3, subsequently, and finally on the data region S12.

Similar to the subset number, the repetition number is a parameter in an OSEM method. That is, the repetition number is a number of counts of calculating the evaluation value to the data region of the detector ring 12. In Embodiment 1, the repetition number is preferably 1 from a requirement for enhanced speeds.

The three-dimensional reconstruction data generated by the preview image generating section 22a is converted into an MIP (maximum intensity projection) image. Description will be given of the MIP image. The preview image generating section 22a selects the maximum pixel value of a line L crossing the three-dimensional reconstruction data. Specifically, the preview image generating section 22a selects a pixel N having the maximum luminance among each of diagonally shaded pixels in FIG. 5 of the three-dimensional reconstruction data. The preview image generating section 22a places the value of the pixel N on a position representing a point p on a plane F.

Figure 5:
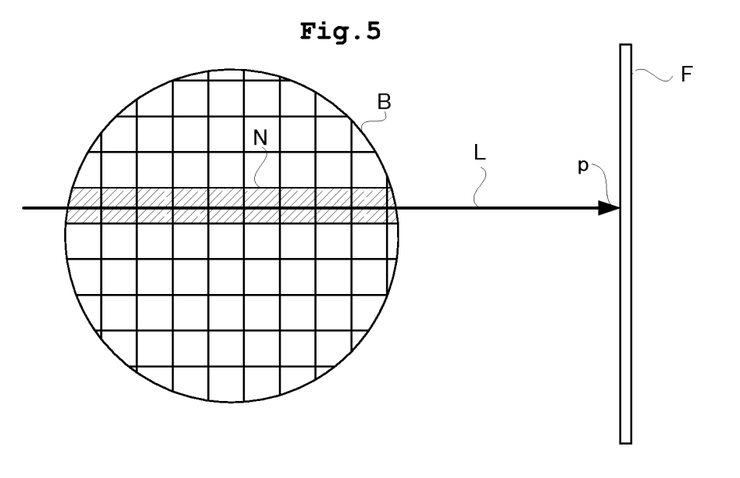
FIG. 5 is a schematic view illustrating an MIP image according to Embodiment 1.

The preview image generating section 22a repeatedly performs such operations while moving the point p on the plane F (plane of projection). The preview image generating section 22a changes a line L for every operation to select a pixel having the maximum luminance (luminance indicating that the most annihilation gamma-ray pairs are generated). The line L is always orthogonal to the plane F while it is moved. The values of the selected pixels are successively placed on the plane F, whereby the MIP image is generated on the plane F. The MIP image is a preview image Pa generated by the preview image generating section 22a.

Description will be given of a reason for adopting the preview image as an MIP image. The MIP image is suitable as one image for understanding how the generating sources of the annihilation gamma-ray pairs are distributed in the entire field of view of the three-dimensional radiation tomography apparatus 9. Consequently, the MIP image is suitable for understanding the condition of the breast B in the field of view of the radiation tomography apparatus 9. In addition, radiopharmaceutical is somewhat likely to be accumulated in the skin of the subject. Accordingly, a contour of the subject appears in the MIP image. This is advantageous for understanding the shape of the breast B in the field of view of the radiation tomography apparatus 9.

The preview image generating section 22a maps the generating sources of the annihilation gamma-ray pairs detected during the image generation time t, thereby generating the preview image Pa. The image generation time t is preferably in a range of 1 second to 1 minute, and more preferably approximately 10 seconds. The preview image generating section 22a successively generates the MIP image for every image generation time t.

The tomographic image generating section 22b generates the tomographic image Pb when the inner hole of the detector ring 12 is cut along a plane in accordance with the list data outputted from the coincidence unit 21. The tomographic image Pb is a diagnostic image with the generating sources of the annihilation gamma-ray pairs being mapped therein. The tomographic image generating section 22b generates the tomographic image Pb through the successive approximation reconstruction method. Here, the tomographic image Pb is generated with the use of every detection data outputted from the detector ring 12. When the breast B of the subject is aligned during inspections, detection data detected from completion of the alignment to completion of detecting the annihilation gamma-ray pairs is all used for generating the tomographic image Pb. The tomographic image generating section 22b corresponds to the diagnostic image generating device in the present invention.

A display unit 36 displays the image generated by the preview image generating section 22a or the tomographic image generating section 22b. A console 35 inputs various operations by an operator to the radiation tomography apparatus 9. A memory unit 37 stores every data and parameter. The data such as detection data from the detector ring 12, coincidence data from the coincidence unit 21, the preview image Pa, and the tomographic image Pb is generated by an operation of each element, and the parameter is referred upon the operation of each element. The console 35 corresponds to the input device in the present invention. The display unit 36 corresponds to the display device in the present invention.

The radiation tomography apparatus 9 includes a main controller 41 configured to control each element en bloc. The main controller 41 has a CPU, and provides each element 19, 20, 21, 22a, and 22b by executing various programs. The above elements may each be divided into a controller that performs their functions.

<Operation of Radiation Tomography Apparatus>

Figure 6:
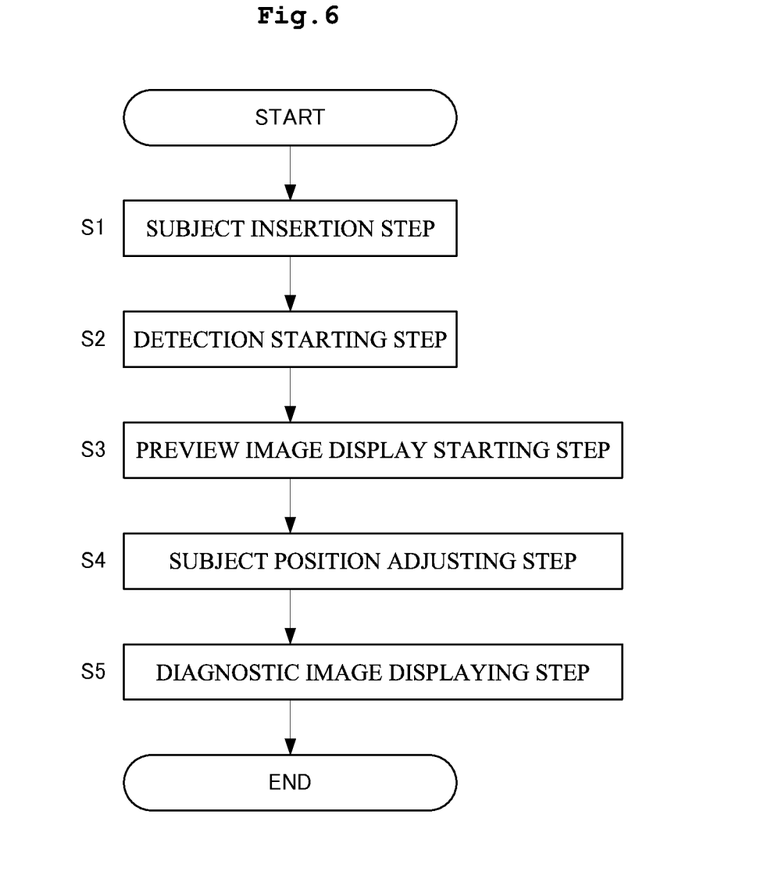
FIG. 6 is a flow chart illustrating operations of the radiographic apparatus according to Embodiment 1.

Description will be given next of operations of the radiation tomography apparatus 9. As illustrated in FIG. 6, the radiation tomography apparatus 9 according to Embodiment 1 conducts diagnosis to a subject by inserting a breast B of a subject M into an inner hole of a detector ring 12 (subject insertion step S1), and then detection of an annihilation gamma-ray pair starts (detection starting step S2). Thereafter, displaying a preview image Pa starts (preview image display starting step S3), and then a position of the subject is adjusted (subject position adjusting step S4). Finally, a diagnostic image is displayed on a display unit 36 (diagnostic image displaying step S5). Description will be given hereinafter of each of these steps.

<Subject Insertion Step S1>

Radiopharmaceutical is administered in advance to the subject. When distribution of the radiopharmaceutical within the subject is stable to some extent, the breast B of the subject is inserted into the inner hole of the detector ring 12. Here, the breast B of the subject is deeply guided into the detector ring 12 so as the breast to be entirely contained in the field of view of the radiation tomography apparatus 9.

<Detection Starting Step S2, and Preview Image Display Starting Step S3>

When an operator issues a command via the console 35 to the radiation tomography apparatus 9 to start tomographic radiography, the detector ring 12 starts to send detection data. The detection data is sent to the preview image generating section 22a via the filter 20 and the coincidence unit 21. The preview image generating section 22a generates a preview image Pa as an MIP image successively for every image generation time t (of 1 second to 1 minute). The generated preview image Pa is successively displayed on the display unit 36. That is, the preview image generating section 22a generates the preview image Pa successively that is updated for every image generation time t. The preview image generating section 22a generates the preview image Pa using the detection data on the annihilation gamma-ray pair detected by the detector ring 12 within the image generation time t. Consequently, an appearance of the breast B of the subject in the radiation tomography apparatus 9 can be checked sequentially upon comparison of the preview images Pa updated successively. As a result, the preview image Pa displayed on the display unit 36 is to be updated for every image generation time t.

<Subject Position Adjusting Step S4>

The operator confirms how the breast B of the subject is contained in the detector ring 12 in accordance with the preview image Pa. When the operator confirms from the preview image Pa that the breast B of the subject is contained in the detector ring 12 without any problems, an annihilation gamma-ray pair is continuously detected to generate the tomographic image Pb. In the description about the operations, description will be given of the case where the breast B has to be aligned because the breast B is contained in the inner hole of the detector ring 12 less deeply or the annihilation gamma-ray pair is generated at an edge of the field of view of the radiation tomography apparatus 9.

When confirming from the preview image Pa that the breast B has to be aligned, the operator issues a command via the console 35 to the radiation tomography apparatus 9 to stop radiation detection. The detector ring 12 stops radiation detection upon receiving the command to stop radiography from the operator. Thereafter, the operator aligns the breast B to the detector ring 12, and then issues a command via the console 35 to the radiation tomography apparatus 9 to resume radiography. Accordingly, the display unit 36 displays the preview image Pa with the aligned breast B appearing therein, allowing the operator to confirm whether or not a position of the breast B is suitably adjusted.

<Diagnostic Image Display Step S5>

Radiation is continuously detected until a satisfactory number of pieces of detection data for generating the diagnostic image is obtained. The detector ring 12 stops radiation detection with the satisfactory number of pieces of detection data. The detection data is then sent to the tomographic image generating section 22b. The display unit 36 displays the tomographic image Pb generated by the tomographic image generating section 22b, and an inspection is completed.

Description will be given of the detection data used for generating the tomographic image by the tomographic image generating section 22b. When the breast B of the subject is aligned during radiation, the shapes of the breast B prior and subsequent to the alignment are different. Accordingly, the detection data obtained prior to stopping radiography for the alignment cannot be used for generating the tomographic image Pb. The tomographic image generating section 22b generates the tomographic image Pb using only the detection data subsequent to the alignment. That is, the tomographic image generating section 22b generates the tomographic image Pb using the detection data obtained after the operator issues a command to resume radiography. The tomographic image generating section 22b does not use the detection data obtained before a command to resume radiography is issued for generating the tomographic image Pb.

At this time, the tomographic image generating section 22b can select whether or not to use the detection data for generating the tomographic image Pb, the detection data being obtained firstly after the alignment for generating the preview image Pa.

As noted above, Embodiment 1 includes the preview image generating section 22a configured to generate the preview image Pa during radiography. The operator can confirm from the preview image Pa how the subject appears in the radiation tomography apparatus 9 also during radiography. When the position of the subject in the field of view is not suitable for diagnosis, the operator can stop radiation detection of the detector ring 12 via the console 35. That is, the radiography can be stopped before a diagnostic image Pb having a suitable level of clearness for diagnosis is generated, and the radiography of the diagnostic image Pb can be resumed after the subject is aligned. Consequently, diagnosis with higher accuracy can be conducted, and a shorter additional imaging time is achieved even when radiography is resumed. As a result, the radiation tomography apparatus 9 having suppressed burden to the subject can be provided.

With the foregoing construction, the diagnostic image generating section 22b generates the tomographic image Pb for diagnosis also using the detection data that the preview image generating section 22a has been used for generating the preview image Pa. This increases the number of pieces of detection data as much as possible upon generating the tomographic image Pb, achieving the radiation tomography apparatus 9 that allows generating the clearer tomographic image Pb.

With the foregoing construction, the preview image Pa is updated for every time t for image generation. Such the construction allows the operator to recognize sequentially how the subject appears in the field of view of the radiation tomography apparatus currently. This enables radiography of the tomographic image with movement of the subject being monitored.

The breast B is soft and thus has a non-uniform shape. In addition, a breast inspection adopts a mode of guiding the subject partially into the detector ring 12 to obtain a tomographic image. Accordingly, the mode has a possibility of failing to guide the breast B of the subject into the radiation tomography apparatus 9 suitably, the possibility being higher than a radiation tomography apparatus guiding a subject entirely into the detector ring. Consequently, application of the construction of Embodiment 1 to the radiation tomography apparatus 9 for breast inspections achieves radiography of the breast B efficiently.

The present invention is not limited to the foregoing configurations, but may be modified as follows.

(1) The preview image generating section 22a according to the above embodiment uses the list mode OSEM. Instead of this, the preview image Pa may be generated by a statistical technique with the use of list mode DRAMA (Dynamic Row-Action Maximum Likelihood Algorithm).

(2) The image reconstruction method in the above embodiment uses the statistical reconstruction technique. Alternatively, the preview image Pa may be generated, as is conventionally done, by a back projection method in accordance with sinogram data.

(3) In the above embodiment, the preview image generating section 22a uses the MIP image as the preview image Pa. Instead of this, a two-dimensional planar image may be used as the preview image Pa. As illustrated in FIG. 5, the MIP image is generated by placing pixels of a line crossing the three-dimensional data with the maximum luminance on the plane F. Here, the two-dimensional planar image is generated by summing all the pixels of a line crossing the three-dimensional data to obtain a total value and placing the total value on the plane F. The two-dimensional planar image allows expression of the radiopharmaceutical distribution with less influence of noises than the MIP image.

Figure 7:
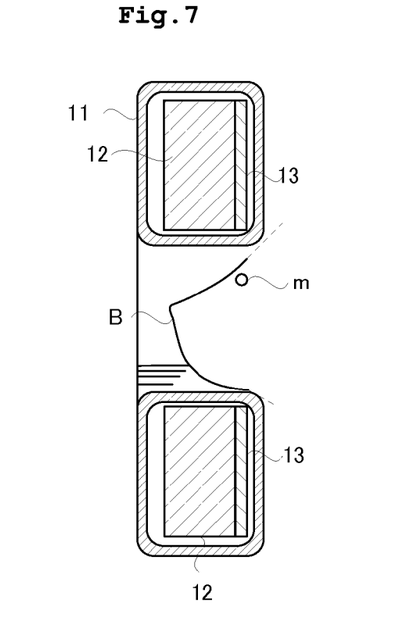
FIG. 7 is a schematic view illustrating a marker according to one modification of the present invention.

(4) In the above embodiment, diagnosis may be conducted with a marker attached to the breast B. Specifically, as illustrated in FIG. 7, a metal marker m absorbing radiation is attached to the breast B of the subject before guiding the breast B into the detector ring 12 to take the tomographic image Pb. Such may be adopted. The preview image Pa contains an image of the marker m. This allows the operator to check easily an area in the field of view where the breast B to be imaged exists. A point source of emitting radiation may be used as the marker instead of a metal. As for a nuclide of radioactive material in the point source, it is more preferable to select a nuclide that emits gamma-rays similar to an annihilation gamma-ray pair in physical property. As noted above, the marker m attached to the subject allows the operator to easily confirm the position of the subject in the field of view of the radiation tomography apparatus 9 by merely checking how the marker m appears in the preview image Pa.

(5) In each of the foregoing embodiments, the scintillation counter crystal is composed of LYSO. Alternatively, the scintillation counter crystal composed of another material, such as GSO ($Gd_2SiO_5$), may be used in the present invention. This modification allows provision of a radiation detector of low price.

(6) The light detector in each of the foregoing embodiments is constituted by the photomultiplier tube. The present invention is not limited to this embodiment. Instead of the photomultiplier tube, a semiconductor detector such as a photodiode, an avalanche photodiode, and a silicon photomultiplier may be used.

(7) In each embodiment mentioned above, the detector ring 12 is an O-shaped ring. Instead of this, the detector ring 12 may be a C-shaped arc.

INDUSTRIAL APPLICABILITY

As noted above, the present invention is suitable for radiation tomography apparatus for medical uses.

REFERENCE SIGNS LIST m marker
Pa preview image
P0 diagnostic image
t image generation time
CT image generation count number
12 detector ring
22a preview image generating section (preview image generating device)
22b tomographic image generating section (diagnostic image generating device)
35 console (input device)
36 display unit (display device)

The invention claimed is:

1. A radiation tomography apparatus comprising:
   a detector ring having radiation detectors for detecting radiation, the radiation detectors being arranged annularly;
   an input device configured to receive a stop command to temporarily stop the detection ring detecting radiation and configured to receive a resuming command to resume the detection ring detecting radiation;
   a preview image generating device configured to generate a plurality of first preview images successively one for every image generation time during a detecting radiation session before the input device receives the stop command in accordance with first detection data generated from the detector ring before the input device receives the stop command, and configured to generate a plurality of second preview images successively one for every image generation time during the detecting radiation session after the input device receives the resuming command in accordance with second detection data generated from the detector ring after the input device receives the resuming command, each preview image having a generating source of an annihilation radiation-pair mapped therein;
   a diagnostic image generating device configured to map the generating source of the annihilation radiation-pair and configured to generate a diagnostic image after the detector ring completes the detecting radiation session based on the second detection data without using the first detection data when the input device has received the stop command during the detecting radiation session and based on the first detection data when no stop command has been received during the detecting radiation session; and
   a display device configured to display the preview images or the diagnostic image.

2. The radiation tomography apparatus according to claim 1, wherein the diagnostic image generating device is configured to generate the diagnostic image using the detection data that the preview image generating device has used for generating the plurality of second preview images when the input device has received the stop command during the detecting radiation session and configured to generate the diagnostic image using the detection data that the preview image generating device has used for generating the plurality of first preview images when the input device has received no stop command during the detecting radiation session.

3. The radiation tomography apparatus according to claim 1, wherein the preview image generating device has the image generation time of one second to one minute.

4. The radiation tomography apparatus according to claim 1, wherein:
   the preview image generating device generates the preview images from the detection data by a statistical reconstruction technique, and
   a number of subsets in the form of a parameter in the statistical reconstruction technique is in a range of 2 to 600, and a number of occurrences representing iteration in the statistical reconstruction technique is in a range of 1 to 16.

5. The radiation tomography apparatus according to claim 1, further comprising a marker attached to the subject and configured to absorb radiation.

6. The radiation tomography apparatus according claim 1, wherein the radiation tomography apparatus is used for breast inspections.

7. A method of providing a diagnostic image of a body part using a radiation tomography apparatus comprising:
   receiving detection data generated from a detector ring having radiation detectors for detecting radiation, wherein the radiation detectors are arranged annularly;
   generating at least one preview image during a detecting radiation session of the radiation tomography and prior to the completion of the detecting radiation session;
   displaying the at least one preview image during the detecting radiation session;
   temporarily stopping the detecting radiation session based on a stop command received by an input device;
   resuming the detecting radiation session based on a resume command received by the input device;
   generating a diagnostic image of the body part, after the detecting radiation session of the radiation tomography apparatus has been completed, based on the detection data generated after the resuming of the detecting session without the detection data generated prior to the temporarily stopping of the detecting session; and
   displaying the diagnostic image of the body part.

* * * * *